United States Patent
Kershman et al.

(10) Patent No.: US 6,241,997 B1
(45) Date of Patent: *Jun. 5, 2001

(54) CHEWABLE CALCIUM SUPPLEMENT AND METHOD

(75) Inventors: Alvin Kershman, Paradise Valley; Jeff Lynn Shear, Chesterfield, both of MO (US); Ronald David Mogel, Indian Wells, CA (US)

(73) Assignee: SMTM Group. LLC, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/042,495

(22) Filed: Mar. 16, 1998

(51) Int. Cl.[7] .................................................. A61K 9/68
(52) U.S. Cl. ..................... 424/440; 424/48; 424/441; 424/442; 426/3; 426/4; 426/5; 426/6
(58) Field of Search ................... 424/442, 440, 424/441, 48; 426/660, 3–6

(56) References Cited

U.S. PATENT DOCUMENTS

| | | | |
|---|---|---|---|
| 3,253,988 | 5/1966 | Scott | 167/55 |
| 3,901,977 | 8/1975 | Rebane | 426/146 |
| 4,609,543 | 9/1986 | Morris et al. | 424/38 |
| 5,552,163 | * 9/1996 | Hartman et al. | 426/3 |
| 5,776,536 | * 7/1998 | Tremblay et al. | 426/660 |

FOREIGN PATENT DOCUMENTS

| | | |
|---|---|---|
| 0753302A1 | 1/1997 | (EP) . |
| 689722 | 4/1953 | (GB) . |
| 2266217 | 10/1993 | (GB) . |
| 61019457 | 1/1986 | (JP) . |

* cited by examiner

Primary Examiner—F. T. Moezie
(74) Attorney, Agent, or Firm—Michael Pritzkau; Stephen C. Shear

(57) ABSTRACT

A chewable calcium composition and its associated method of manufacturing are disclosed. The chewable composition includes a lipid base and a micronized calcium salt substantially uniformly mixed with the lipid base such that the lipid base forms a continuous phase. The composition provides for a relatively large dose of calcium in a easy to take chocolate like, chewable form. The composition of the present invention is manufactured by providing the lipid base including a melting temperature. The lipid base is then heated to a temperature of approximately 120° F. such that the lipid base melts. After the lipid base melts, the micronized calcium salt is mixed with the lipid base to form a melted mixture such that the micronized calcium salt is substantially uniformly distributed in the melted lipid base. Thereafter, the melted mixture may be tempered in a predetermined way before causing the mixture to solidify and then molded into chewable portions, each of which includes a predetermined amount of calcium salt. In one aspect of the invention, a predetermined portion of xylitol may be added to the melted mixture such that the xylitol is substantially uniformly distributed in the melted mixture. When the composition is consumed, the xylitol provides for salivation within the oral cavity leading to substantially rapid dissolution of the composition therein so as to provide taste and texture characteristics which are akin to those of chocolate.

31 Claims, 1 Drawing Sheet

CHEWABLE CALCIUM SUPPLEMENT AND METHOD

BACKGROUND OF THE INVENTION

The present invention relates generally to a chewable calcium supplement and more particularly to a chewable calcium supplement including a lipid base. An associated method of manufacturing is also disclosed. The supplement and method are particularly suited to provide a calcium salt in a concentration of 50 percent or greater while maintaining a satisfying chocolate like taste.

The average adult requires a daily intake of calcium in the range of 1,000 to 1,400 mg of calcium. Such a calcium intake is provided by drinking approximately one quart of milk daily. Few adults are willing to drink this quantity of milk. Of course, adequate intake of calcium can be maintained by careful dietary planning. Unfortunately, most consumers are unable to ensure such careful diet coordination. For this reason and due to increasing awareness of the importance of adequate calcium intake, various forms of calcium supplementation have been developed. Calcium salts such as, for example, calcium carbonate are a rich form of calcium supplementation. Adequate intake of calcium is provided by daily consuming approximately 2–4 grams of a calcium salt. One relatively successful method of providing a calcium salt has been to add the salt to orange juice. The latter, for the most part, successfully eliminates the unpleasant chalky texture or taste which is typically associated with the direct consumption of calcium salts.

Another prior art form of calcium supplementation is the provision of chewable tablets. The latter usually provide approximately 400 to 600 mg of calcium per tablet. Thus, several doses are required to provide the required daily amount. Again, the major problem with chewable forms resides in the unpleasant, but inherent chalky taste of calcium salts.

Of course, calcium is also provided in non-chewable tablet form. Although this form is appropriate, many consumers prefer the chewable form of supplementation. Often, the consumer must swallow a plurality of tablets in order to receive an adequate daily calcium intake.

The present invention provides a chewable calcium supplement and method of manufacture which is capable of providing an adequate daily calcium intake in a single dose. The supplement approaches the characteristics of a pleasant chocolate which readily melts in the consumer's mouth in an anticipated and satisfying fashion.

SUMMARY OF THE INVENTION

A chewable calcium composition and its associated method of manufacturing are disclosed. The chewable composition includes a lipid base and a micronized calcium salt substantially uniformly mixed with the lipid base such that the lipid base forms a continuous phase. The composition provides for a relatively large dose of calcium in a easy to take, chocolate like chewable form.

The composition of the present invention is manufactured by providing the lipid base such that the latter has a melting temperature. The lipid base is then heated to a temperature of approximately 120° F. such that the lipid base melts. After the lipid base melts, micronized calcium salt is mixed with the lipid base to form a melted mixture such that the micronized calcium salt is substantially uniformly distributed in the melted lipid base. Thereafter, the melted mixture is caused to solidify and then molded into chewable portions, each of which includes a predetermined amount of calcium salt.

In one aspect of the invention, a predetermined portion of xylitol is added to the melted mixture such that the xylitol is substantially uniformly distributed in the melted mixture. When the composition is consumed, the xylitol provides for salivation within the oral cavity leading to substantially rapid dissolution of the composition therein so as to provide taste and texture characteristics which are akin to those of chocolate.

BRIEF DESCRIPTION OF THE DRAWING

The present invention may be understood by reference to the following detailed description taken in conjunction with the drawing briefly described below.

DETAILED DESCRIPTION OF THE INVENTION

Figure 1:
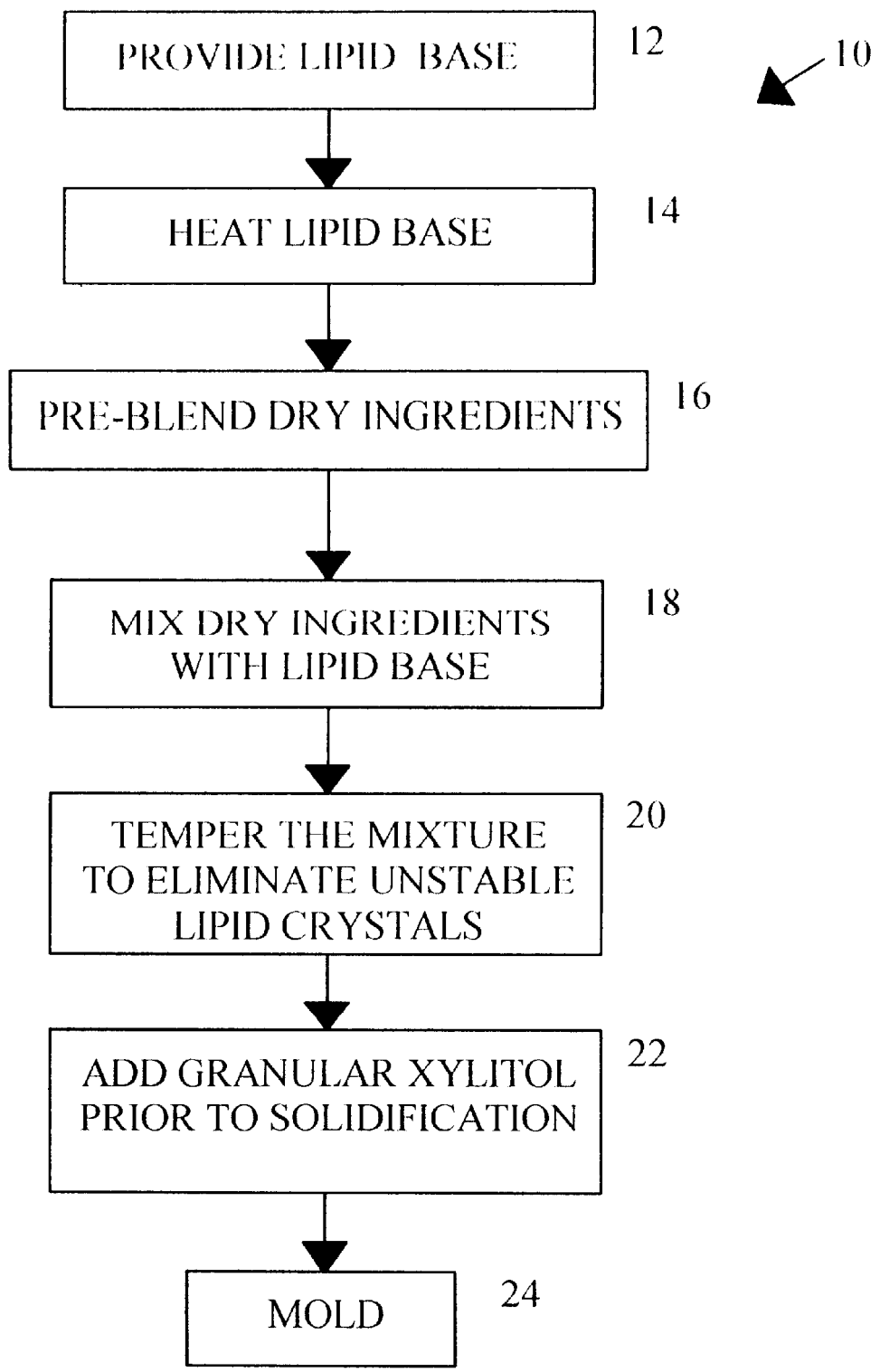
FIG. 1 is a flow diagram which illustrates a method of manufacturing a calcium composition supplement in accordance with the present invention.

Attention is immediately directed to FIG. 1, which illustrates the method of the present invention, generally indicated by the reference numeral 10, for manufacturing a chewable calcium supplement. Method 10 begins with a step 12 in which a lipid base is provided. The lipid base may comprise a vegetable oil base commonly known as hard butter. Hard butters are hydrogenated, press fractionated or other processed oils that are processed or recombined to have a solid fat index (percent solid fat vs. temperature) similar to that of cocoa butter. One alternative to a hard butter is cocoa butter, however, any suitable lipid base may be utilized in accordance with the teachings herein, keeping in mind that the primary objective is for the lipid base to be relatively hard or solid at room temperature, but to melt rapidly in the mouth at a temperature of approximately 92° F. to 98° F. It should be noted that such a rapid melting effect is, at least in part, responsible for chocolate's uniquely satisfying eating characteristics.

Continuing to refer to step 12 of FIG. 1, the final formula of the calcium supplement will contain approximately 20 to 50% hard butter by weight with 35% by weight being a practical use level. However, the process starts with 100% hard butter treated with an appropriate surfactant that minimizes the surface tension of the oil, allowing it to oil wet and encapsulate non-oil soluble materials. Appropriate surfactants are known in the art and may include, but are not limited to lecithin or glycerol monostearate.

At step, 14 the lipid base is heated to approximately 110–120° F. to eliminated any lipid crystal structure that may exist in the initial solid form. This temperature will be maintained throughout the manufacturing process up until all solid ingredients are added in a latter step.

In step 16, separate from the lipid base, dry ingredients (primarily a calcium salt) are pre-blended from materials that have been either pulverized or processed to have a particle size less than 50 microns. This particle size is selected since particle having a size greater than 50 microns are easily detected by tactile sensors in the tongue of a person and would not be smooth as is expected in chocolate. Since the calcium salt is the primary ingredient, it is particularly important that its particle size is less than 50 microns.

With step 18, the pre-blended dry ingredient mixture is gradually added to the heated lipid base until a high solid suspension is obtained. That is, 50% to 80% solids by weight. It should be noted that suspended solids are limited by a maximum volume that will pack in a continuous phase; approximately 74% internal phase by volume. Slow addition of the dry ingredients is critical in the production of the composition to insure that the solid particles are suspended in their micronized state and not as agglomerated clumps. Moreover, rapid addition can cause the mixing process to fail in that the melted mixture will not have the finished flow properties or characteristics as expected in a chocolate products but instead be a granular oily mass (a sign of product failure).

Mixing step 18 is accomplished in a heated mixing device that insures thorough mixing of all materials (proper circulation) with minimal shear, i.e. a planetary mixer or similar device. In this regard, low shear mixers with high shear dissipaters are suitable for use in this step, but are most appropriate for large volume operations. Therefore, the optimum mixing device may be a medium to low shear type planetary mixer or a scrape surface mixer having secondary mix rotating in an opposite direction to the scraper so as to simulate planetary mixing.

It is important to understand that a key difference between the calcium composition of the present invention and actual chocolate is the absence of sugar and milk. Though a small amount of sugar and milk could be utilized in the formula, it is not necessary. Therefore, sugar and milk solids, normally found in chocolate confections, can be replaced by micronized calcium salts so as to further contribute to the rich calcium content of the composition of the present invention. Calcium carbonate is considered as a primary calcium source by this invention, but any other suitable salts may be used such as, for example, calcium phosphate or calcium citrate.

Still discussing mixing step 18, along with the calcium salt are added flavoring ingredients as well as cocoa for an imitation chocolate formulation. Moreover, vitamin D and other actives can be included. The cocoa may be low fat or normal fat. In most instances, it may be desired to provide sweetness using an artificial sweetener such as, for example, aspartame. The latter is acceptable for the formulation since the waterless mixture will not degrade the aspartame. Other additives may include milk flavors as well as the addition of vanilla and salt which are commonly found in normal confection formulas. It should be noted that alternate formulas can be produced without the presence of cocoa that would allow for either higher levels of calcium (60%–70%) or other actives. These alternate formulas may be flavored with imitation cocoa concentrates or any other suitable flavors such as, for example, orange or lemon. Moreover, formulas may be colored using any suitable coloring including artificial colors. While sugar can be used, the presence of sugar is considered to be an undesirable ingredient in a calcium supplement system for the reason that consumers having sugar restricted diets such as, for example, diabetics may consume a non-sugar containing supplement.

After having added all dry ingredients, a suspension results which contains anywhere from 60 to 70% or more solids in a continuous oil phase. This high solids suspension now exhibits non-Newtonian rheological properties that are quite different from the initial oil and are normally defined as thixotropic. Using appropriate surfactants and mixing techniques, the product can be formed as rheologically pseudoplastic or essentially a solid liquid depending on the intended result. It is mentioned that both thixotropes and pseudoplastics require initial high shear before flowing or exhibiting Newtonian characteristics. However, since the mixing is constant in step 18 the melted mixture will readily flow from the container.

Turning to step 20, after completion of the addition of solid ingredients and a minimal mixing time, the mixture is tempered. Tempering is the process of cooling the continuous oil phase below its melting point and then bringing it back to the melting point and reversing the process several times until unstable lipid crystals are basically eliminated. In this manner formation of optimum crystal structures is insured (i.e., beta prime crystals vs. alpha or beta crystals). As an alternative to using a planetary mixer, tempering can also be accomplished continuously using a swept surface heat exchanger. Also, hard butters can be formulated to minimize or eliminate tempering in order to form a stable lipid crystal structure.

Following tempering, it is to be understood that the mixture may be solidified or molded to form individual doses. The result is an acceptable chewable calcium supplement. However, because the typical mixture does not contain sugars or other humectants, salivation is not stimulated. In this instance, upon consumption of the supplement, the lack of salivation stimulation will result in a period of time in the oral cavity during which the composition will seem to stick to the oral cavity tissue. This may result in a negative perception by the consumer. As will be seen immediately hereinafter, the present invention solves the salivation stimulation problem in a highly advantageous manner.

Still referring to FIG. 1, in step 20, granular xylitol is added to the tempered mixture produced by step 20 prior to solidification of the mixture. The xylitol should be granular (20 to 100 mesh size) as opposed to micro pulverized (less than 50 M or through a 350 mesh screen). Thus, the xylitol particles to be suspended will range in size from approximately 150 to 900 microns whereas the calcium salt added to the compound ranges in size from approximately 10 to 50 microns.

In step 22, the composition including the xylitol is molded into appropriate dosages which typically deliver a full day's recommended calcium intake in a single dose.

When the molded final product is placed in the mouth, the xylitol particles are readily detectable and will, in fact, crunch when chewed. Additionally, the xylitol will dissolve rapidly. Dissolution of the xylitol causes the oral cavity to salivate rapidly. The increase in salivation eliminates any negative perception associated with the clinging effect of the low or no humectant containing compound. The result is a highly advantageous and heretofore unseen calcium supplement/composition that tastes and feels much like real chocolate with artificial sweeteners providing sweetness characteristics and milk flavor providing milk characteristics. It should be noted that xylitol may, like the calcium salt, be provided in micronized form (mixed with other dry ingredients) and will in this form also serve to aid product dispersion during mastication. However, it has been found that granular xylitol is more efficient for this purpose. It should also be noted that the addition of the xylitol may be performed just prior to tempering step 20 or at some point during the tempering step.

Having generally described the manufacture of the calcium composition of the present invention, as one example of a specific formulation of the composition, which proved to be very acceptable in actual testing, the composition was made up of the following ingredients:

TABLE 1

| INGREDIENT | CONTENT (WEIGHT) |
| --- | --- |
| Palm kernel based hard butter 92° F. MP | 34.5% |
| Lecithin | 1.0% |
| Salt | 0.3% |
| Micronized calcium carbonate | 50.0% |
| Xylitol | 4.0% |
| Cocoa | 9.0% |
| Milk flavor | 0.5% |
| Vanilla (crystalline) | 0.5% |
| Aspartame | 0.2% |

The composition of Table 1 was produced in a batch size of approximately 2,600 gm. Using a Hobart 5 Qt. planetary mixer jacketed with a heating mantel. In accordance with the method of the present invention, all dry ingredients, except the xylitol were thoroughly premixed. The hard butter was melted in the heated mixer to 120° F. Thereafter, the lecithin was added to the melted hard butter. Dry ingredients were added while mixing at low speed for approximately one hour. The heat was reduced and the mixture was allowed to cool. If desired, cooling coils can be utilized.

As the mixture reached a temperature of approximately 100° F., the xylitol was added. The tempering process then began by cooling the mixture to a temperature of 86°–87° F. and then increasing heat until a temperature of 92° F. was reached. Thereafter, the mixture was allowed to cool to 86°–87° F. and then brought back up to 92° F. for at least two more cycles. The mixture was held at 92° F. and mixed for at least one hour (viscosity will increase accordingly). At 92° F. the composition was poured off into appropriate sized molds of approximately 5.8 gm per mold. It should be noted that exact weight of contents is very critical to deliver an accurate dosage of calcium. The molded composition was then placed in cooling tunnel or refrigerated unit at approximately 50° F. for 10 minutes and then held at room temperature (70° F.) for at least 24 hours. De-molding and packaging were then performed. The packaged product should be held at approximately 70° for up to two weeks prior shipment. The longer the product is held at ambient temperature, the more stable the fat crystal structure becomes and, therefore, the harder the product will become. In this manner, the calcium supplement of the present invention was produced providing approximately 1160 mg. of elemental calcium (2900 mg of calcium salt) in each pleasant tasting individual dose.

In one modification of the method of the present invention, a high melting point vegetable stearine can be added to the hard butter to insure shelf stability at higher temperatures. No more than 1%–2% Stearine with a melting point of approximately 150° F. should be added or a waxy effect will result. Stearine is pre-melted and added to the melted lipid phase. In this process, the lipid phase is held at the melting temperature of the stearine when the latter is added to the melted lipid phase. The resulting mixture is held at the higher, stearine melting point until such time that all solids have been added to the mixture. Thereafter, molding and cooling may be performed. It should be mentioned that with the addition of stearine, tempering is not required prior to molding of the mixture. The addition of stearines will prevent the composition from melting after packaging even at temperatures of 100° F. Yet, the composition will be palatable with the anticipated taste and melting characteristics which are associated with chocolate. It is noted that the composition is slightly more palatable without the inclusion of stearine, but provisions must be made to ship the packaged composition in conditioned air such that temperatures do not exceed 85° F.

It should be appreciated that the present invention is highly advantageous in that it provides a confection type calcium delivery system in the form of a heretofore unseen imitation chocolate composition containing a high concentration of calcium carbonate or other calcium salts without the negative aftertaste which is typically associated with such high levels of calcium. Moreover, ingredients such as sugar and milk solids may be replaced in a way which serves to further increase the calcium delivery capabilities of the composition. Specifically, the present invention provides a relatively small and easy to consume calcium product that can contain at least the equivalent calcium of a quart of milk or the daily requirement of over 1,000 mg. of elemental calcium in a 4 to 10 gm. dose.

As another advantage, the size and amount of composition that can be consumed is not dictated by the level of calcium salts and/or elemental calcium required to provide a minimum daily calcium intake since a relatively large amount of calcium is readily contained in a small dosage volume. The concentration of calcium does not effect product palatability. As described above, xylitol allows for greater palatability and ease of consumption.

As still a further advantage, the imitation chocolate calcium supplement of the present invention may be sugar, milk and sorbitol (a caloric sugar substitute normally seen in imitation chocolate) free.

One skilled in the art may devise many alternative formulations for the calcium composition and associated method of manufacturing disclosed herein. Therefore, it should be understood that the present invention may be embodied in many other specific forms without departing from the spirit or scope of the invention and that the present examples and methods are to be considered as illustrative and not restrictive, and the invention is not to be limited to the details given herein, but may be modified within the scope of the appended claims.

What is claimed is:

1. A chewable composition including:
    a) a lipid base;
    b) a micronized calcium salt uniformly mixed with said lipid base to form a continuous phase; and
    c) xylitol particles suspended in the mixture, said xylitol particles including a particle size in the range from approximately 150 to 900 microns.

2. The composition of claim 1 wherein said micronized calcium salt is made up of particles having a size ranging from approximately 10 to 50 microns.

3. The composition of claim 1 wherein said lipid base includes a melting temperature which provides for melting of the composition in a person's mouth.

4. The composition of claim 3 wherein said melting temperature is approximately 92° F.

5. The composition of claim 1 wherein said lipid base includes a hard butter.

6. The composition of claim 1 wherein said lipid base includes a cocoa butter.

7. The composition of claim 1 wherein said calcium salt comprises at least 30% by weight of the composition.

8. The composition of claim 1 wherein said calcium salt is calcium carbonate.

9. The composition of claim 1 including cocoa uniformly mixed with said lipid base.

10. The composition of claim 1 including an artificial sweetener uniformly mixed with said lipid base.

11. The composition of claim 1 including a flavoring uniformly mixed with said lipid base.

12. The composition of claim 11 wherein said flavoring includes a vanilla flavoring.

13. The composition of claim 11 wherein said flavoring includes a milk flavoring.

14. The composition of claim 1 including approximately 1.5% stearine having a melting point of approximately 150° F.

15. A chewable composition consisting essentially of:
   a) a palm kernel based hard butter having a melting point of approximately 92° F.;
   b) lecithin;
   c) micronized calcium salt;
   d) salt;
   e) cocoa;
   f) milk flavor;
   g) crystalline vanilla;
   h) aspartame; and
   i) xylitol particles suspended throughout the composition, said xylitol particles including a particle size in the range from approximately 150 to 900 microns to initiate salivation causing the dissolution of the lipid base and calcium salt mixture.

16. The composition of claim 15 including by weight 34.5% of said palm kernel based hard butter, 1.0% of said lecithin, 50.0% of said micronized calcium salt, 0.3% of said salt, 4.0% of said xylitol, 9.0% of said cocoa, 0.5% of said milk flavor, 0.5% of said crystalline vanilla and 0.2% of said aspartame.

17. The composition of claim 15 wherein said calcium salt is calcium carbonate.

18. A method of manufacturing a chewable composition comprising the steps:
   a) providing a lipid base and heating said lipid base to its melting temperature to melt the lipid base;
   b) mixing the melted lipid base while adding a micronized calcium salt to form a melted mixture;
   c) suspending xylitol particles in the mixture, said xylitol particles including a particle size which is in a range from approximately 150 to 900 microns; and
   d) before causing said melted mixture to solidify, molding the mixture into chewable portions whereby direct contact between the xylitol particles in the mixture and a person's oral cavity initiates salivation causing the dissolution of the mixture.

19. The method of claim 18 wherein said temperature is approximately 120° F.

20. The method of claim 18 wherein step c includes the step of tempering the mixture.

21. The method of claim 20 wherein the melting temperature of said lipid base causes the lipid base to melt in a person's mouth and wherein said tempering step includes the steps of
   i) cooling the melted mixture to a temperature of approximately 100° F.,
   ii) adding said xylitol particles to the melted mixture while remixing the mixture causing the xylitol particles to uniformly distribute in the melted lipid base while maintaining the range of particle size of the xylitol particles.

22. The method of claim 21 wherein the melting temperature of the lipid base is approximately 92° F. and wherein said tempering step further includes the steps of
   iii) cooling the mixture to approximately 8620 F., and
   iv) heating the mixture to a temperature of approximately 92° F.

23. The method of claim 22 wherein said tempering step further includes the step of:
   v) repeating steps (iii) and (iv) at least two additional times.

24. The method of claim 23 wherein said tempering step further includes the step of:
   vi) holding the mixture at approximately 92° F. for at least one hour while remixing the mixture causing the viscosity of the mixture to increase.

25. The method of claim 18 wherein said calcium salt is added to comprise at least 50% by weight of the composition.

26. The method of claim 18 wherein said calcium salt is pulverized to have a calcium particle size in a range of approximately 10 to 50 microns.

27. The method of claim 18 wherein step c includes the step of adding cocoa to the melted mixture causing the cocoa to uniformly distribute in the melted lipid base.

28. The method of claim 18 wherein said mixing step includes the step of adding a flavoring to the melted mixture causing the flavoring to uniformly distribute in the melted lipid base.

29. The method of claim 18 further comprising adding a stearine wherein a melting temperature of the stearine is higher than the melting temperature of the lipid base and said method further includes the steps of (i) melting said stearine, and before said mixing step, (ii) adding the melted stearine to the melted lipid base.

30. In a chewable composition including a lipid base having a micronized calcium salt uniformly mixed with said lipid base, the improvement comprising:
   xylitol particles suspended in the lipid base and calcium salt mixture, said xylitol particles including a particle size in the range from approximately 150 to 900 microns to initiate salivation causing the dissolution of the mixture.

31. In the manufacture of a chewable composition including a lipid base having a micronized calcium salt uniformly mixed with said lipid base, the improvement comprising the step of:
   suspending xylitol particles in the lipid base and calcium salt mixture, said xylitol particles including a particle size in the range from approximately 150 to 900 microns to initiate salivation to cause the dissolution of the mixture.

* * * * *